United States Patent
Kostrzewa et al.

(10) Patent No.: US 7,160,680 B2
(45) Date of Patent: Jan. 9, 2007

(54) MUTATION ANALYSIS BY MASS SPECTROMETRY USING PHOTOLYTICALLY CLEAVABLE PRIMERS

(75) Inventors: Markus Kostrzewa, Borsdorf-Panitzsch (DE); Thomas Fröhlich, Leipzig (DE); Thomas Wenzel, Leipzig (DE); Andres Jäschke, Berlin (DE); Felix Hausch, Stanford, CA (US)

(73) Assignee: Bruker Saxonia Analytik GmbH, Leipzig (DE)

( * ) Notice: Subject to any disclaimer, the term of this patent is extended or adjusted under 35 U.S.C. 154(b) by 130 days.

(21) Appl. No.: 10/079,043

(22) Filed: Feb. 20, 2002

(65) Prior Publication Data

US 2002/0187493 A1 Dec. 12, 2002

(30) Foreign Application Priority Data

Feb. 22, 2001 (DE) ......................... 101 08 453

(51) Int. Cl.
*C12Q 1/68* (2006.01)
*C12P 19/34* (2006.01)

(52) U.S. Cl. ........................................ 435/6; 435/91.1
(58) Field of Classification Search ................ 250/261; 435/6, 91.1; 536/22.1
See application file for complete search history.

(56) References Cited

U.S. PATENT DOCUMENTS

| | | | |
|---|---|---|---|
| 5,547,835 A | * | 8/1996 | Koster ........................... 435/6 |
| 5,830,655 A | * | 11/1998 | Monforte et al. .............. 435/6 |
| 6,043,031 A | | 3/2000 | Köster et al. |
| 6,221,601 B1 | * | 4/2001 | Koster et al. .................. 435/6 |

FOREIGN PATENT DOCUMENTS

| | | | | |
|---|---|---|---|---|
| EP | 0 840 804 B1 | | 5/1998 | |
| WO | WO 97/27325 | * | 7/1997 | ..................... 435/6 |

OTHER PUBLICATIONS

Phillip Ordoukhanian and John–Stephen Taylor, Design and Synthesis of a Versatile Photocleavable DNA Building Block. Application to Phototriggered Hybridization, American Chemical Society 1995, vol. 117, pp. 9570–9571, St. Louis, Missouri.

Sascha Sauer, et al., A novel procedure for efficient genotyping of single nucleotide polymorphisms, Nucleic Acids Research, 2000, vol. 28, No. 5, Oxford University Press, Berlin–Dahlem, Germany.

* cited by examiner

*Primary Examiner*—Kenneth R. Horlick

(57) ABSTRACT

The invention relates to a method of a mass-spectrometric analysis of known mutation sites in the genome, such as single nucleotide polymorphisms (SNPs), using the method of restricted primer extension. The invention consists of the use of primers with a photocleavable linker. The linker creates a gap in a DNA strand which is almost the same size as a natural DNA building block (nucleoside). The linker forms a bridge over a base pair without inhibiting hybridization or enzymatic extension. However, the linker allows the primers to be cleaved after extension in order to obtain short DNA fragments which can be more easily detected on the mass spectrometer.

28 Claims, 2 Drawing Sheets

MUTATION ANALYSIS BY MASS SPECTROMETRY USING PHOTOLYTICALLY CLEAVABLE PRIMERS

FIELD OF THE INVENTION

The invention relates to mass spectrometric analysis of known mutation sites in the genome, such as single nucleotide polymorphisms (SNPs), by primer extension.

BACKGROUND OF THE INVENTION

Subject of this invention is a method for the detection of actual mutative changes in the genome DNA, whereby the possible mutation site has to be known beforehand. These mutative sequence changes may either be a base exchange (point mutation) or the introduction of nucleotides (insertion) or removal of nucleotides (deletion). Point mutations have become particularly well known under the abbreviation SNP (single nucleotide polymorphisms). For humans, is it supposed that there are at least 3 million frequently occurring SNPs which characterize most of the individual differences between humans. They control the individual phenotypes.

For the genome of a species, it is customary to define a "wild type" which is regarded as free of mutation, and a "mutant" which contains a mutation. Considering the frequency of mutations, such as SNPs, and the equal value of mutants and wild types, the definition of the wild type is arbitrary or at least purely accidental.

Nearly all DNA mutations, including all those defined above, produce differences in the mass of the DNA segment containing the mutation in comparison to the mass of a corresponding segment of the wild type. The precise mass determination of a DNA segment can therefore be used for the determination of a mutation.

Mass spectrometry is a very powerful and precise tool for determining the mass of a bio-molecule. By using a mass spectrometric method, such as time-of-flight mass spectrometry (TOF-MS) with ionization by matrix-assisted laser desorption and ionization (MALDI), it is possible to analyze the ions for their masses. However, ionization can also be achieved using electrospray ionization (ESI), in the latter case with mass spectrometers which are generally of a different type.

With polymerase chain reactions (PCR), using a pair of "selection primers", i.e. single strand oligonucleotides about 20 bases long, it is possible to produce double-strand DNA products with a length of at least 40 base pairs in a known way. The mutation site can be incorporated by adequately choosing the sequences of the two selection primers.

The obvious method to simply measure the mass of the PCR-amplified DNA products as such by mass spectrometry, was found to be almost unworkable. The precise measurement of DNA products with more than 40 base pairs proved itself to be almost impossible. The reasons for this are given below. A method therefore had to be found to provide much shorter DNA fragments. To this end, the method of restricted, mutation-dependent primer extension by the use of terminating derivatives of the nucleotide triphosphates has been developed in order to generate extended primers of approximately 15 to 25 nucleotides in length, better suited to identify the nature of the mutation.

This method consists of the following steps: Firstly, a sufficient number of copies of the DNA segment containing the mutation site is produced by PCR using a pair of primary primers. These DNA segments then serve as templates for the enzymatic, mutation-dependent extension of a secondary primer. If in the following the word "primer" is used, always this secondary or extension primer is meant. The extension primer may be identical with one of the two selection primers; however it is regularly much better to use a primer which is not identical.

This primer is a short DNA chain of approximately 15 to 25 nucleotides and functions as a recognition sequence for the site of a possible mutation. The primer is synthesized with a base sequence so that it can be annealed to the template strand as an exact compliment to the base in the vicinity of a known point mutation site. (This form of attachment is known as "hybridization" or "annealing").

In the simplest case, the primer is designed so that it is attached directly neighboring the possible mutation site. The enzymatically controlled extension of this primer by a polymerase is carried out using the dideoxy versions (ddNTP) of the four deoxynucleoside triphosphates (dNTP or, to be precise, dATP, dGTP, dCTP and dTTP). These dideoxynucleoside triphosphates serve as terminators; when built in, they terminate the extension. Which one of the four ddNTPs is inserted depends on the master template: the mutation site is mirrored in a complementary fashion. The four possible terminators differ (as do the associated deoxynucleoside triphosphates) by at least 9 and by a maximum of 40 atomic mass units. In principle, therefore, conclusions about the actual mutation can be made from the mass determination of the primer which has been extended in this way. This method, which always leads to products with the same number of nucleotides, will be referred to in the following as "equal-number-nucleotide primer extension".

Unfortunately, precise determination of the mass of oligonucleotides is difficult. Because of the polyanion character of the DNA, various numbers of ubiquitous sodium (23 atomic mass units) or potassium ions (39 atomic mass units) are particularly likely to attach to the oligonucleotides (instead of the protons), and so-called "adducts" are formed. This uncertainty in the degree to which the adducts are formed makes any precise mass determination exceptionally difficult—at the very least, it means that cleaning has to be extremely thorough and all process parameters have to be carefully monitored for constancy. The equal-number-nucleotide primer extension method is therefore very difficult to use as it is susceptible to error.

Another method of mutation-dependent primer extension has therefore been developed in which the mass difference between the two homozygote forms of the DNA product, i.e. the wild type and the mutant, amounts to at least one nucleotide, i.e. at least approximately 300 atomic mass units. This method will be referred to in the following as "different-number-nucleotide primer extension".

In this case, the primer does not have to hybridize directly next to the possible mutation site. Between the site of the possible mutation and the 3' position of the primer (the position where the primer is extended), the sequence of the template strand may consist of three of the four nucleotides in maximum. The fourth nucleotide appears for the first time at the mutation site. By using, firstly, a polymerase and, secondly, a particular set of unmodified deoxynucleoside triphosphates (dNTP) complementary to the maximum three nucleotides which bridge the 3'-end of the extension primer and the mutation site, and, thirdly, at least one dideoxynucleoside triphosphate (ddNTP) complementary to the fourth type of nucleotide, the primer is extended as a complementary copy at the template. The chain extension is terminated by the dideoxynucleoside triphosphate. Depending on whether a point mutation is present or absent, the polymerase reaction is terminated at the mutation site or is not terminated until the next nucleotide corresponding to a terminator on the other side of the potential mutation site. The extension products of wild type and mutant differ after this different-number-nucleotide primer extension, i.e. they differ in length by at least one nucleotide or by at least approximately 300 atomic mass units. Thus, high mass precision is no longer necessary for determining the mutation type; the difference between the masses of the mutation and the wild type are beyond the range of metal-ion adducts. The mass spectrometric analysis is therefore made considerably easier.

This method of different-number-nucleotide primer extension requires somewhat more elaborate preparation since each of the four types of nucleobases at the mutation site requires its own mixture of dNTPs and ddNTPs. Another disadvantage is the lower degree of multiplexing possible: the number of mutations which can be detected in a single sample at the same time is lower than that for the equal-number-nucleotide primer extension method initially described above. Multiplexing capability is also restricted by the fact that a compatible set of dNTPs and terminators must be found for each reaction to be combined. However, the method has the advantage of being more insensitive to traces of impurities and to changes in the measurement conditions. A further advantage is that there is greater freedom in selecting a site of attachment and this means that the same process conditions for extension can in most cases be maintained because the primer can be designed with greater freedom of choices.

The MALDI preparation and measurement procedure consists of first embedding on a sample support the analyte molecules in a solid UV-absorbent matrix, usually an organic acid. The sample support is then introduced into the ion source of the mass spectrometer. The matrix is then evaporated by a short laser pulse of about 3 nanoseconds, producing a so-called plume consisting of a weakly ionized plasma. This process transports the analyte molecules into the gas phase but, unfortunately, a part of the fragile analyte molecules will be fragmented. The analyte molecules are ionized as a result of collisions with matrix ions of the plume. The voltage which is applied to the ion source apertures accelerates the ions into the flight tube which has no electrical field. Due to their differing masses, the ions are accelerated to different velocities. The smaller ions reach the detector earlier than the larger ions. The flight times are measured and converted into ion masses.

MALDI is ideally suited for the analysis of peptides and proteins. The analysis of nucleic acid chains is somewhat more difficult. Ionization in the case of short-chain nucleic acids in the MALDI process is approximately 100 times less intense than it is for peptides and decreases superproportionally with increasing mass. The reason for this is that only a single proton has to be captured to ionize peptides and proteins. For nucleic acids with multiple negative charges on the poly-anionic sugar-phosphate backbone (one negative charge for each nucleotide), the process to generate singly charged ions has to use such a lot of protons that it is considerably less efficient. The DNA segments (extended primers) which have to be detected must therefore be as short as possible so that they can be detected well.

In a similar way, an ionization method can also be used which uses a solution of the samples as the starting point. This is known as electrospray ionization (ESI). The method is also ideally suited to the detection of peptides and proteins but has similar problems with oligonucleotides. Here also, the oligonucleotides which are to be detected have to be as short as possible.

In MALDI, the choice of the matrix substance plays an important role. There are quite a number of very efficient matrices for the desorption of peptides. Up to now, however, there are only a few efficient matrices for DNA, and they do not solve the sensitivity and adduct problems for DNA.

However, this sensitivity difference can be reduced by chemically modifying the DNA so that it more resembles a peptide. As explained in WO 96/27681 (Gut and Beck), phosphorothioate nucleic acids, for example, where the phosphate groups are replaced by thiophosphate groups, can be converted into a neutrally charged DNA by simple alkylation. This neutrally charged modified DNA can be ionized like a peptide. Adduct formation and fragmentation hardly occur. This modification has made it possible to use matrices which are similar to those used for the desorption of peptides.

In addition to the neutralization, it is also possible to bond a group with a single positive or negative charge (charge tag) covalently to this modified DNA. Attaching a charge means that non-protonating matrices can be used. The use of non-protonating matrix substances leads to an increase in sensitivity for the modified DNA and suppresses the ionization of impurities not carrying a charge. Another advantage of "charge tagging" is the increased stability of the analysis as far as the impurities are concerned which make the detection of unmodified DNA analyte molecules much more difficult.

But even for these modified oligonucleotides, it has been found to be beneficial to keep the segments which are to be analyzed as short as possible.

Using phosphorothioate nucleic acids, a method has been developed for shortening the oligonucleotides whereby a part of the extended primer is digested using an enzyme. This can be achieved by providing only a short chain of nucleotides at the 3' position of the extended primer with thioate groups and not modifying the majority of the nucleotides. The regular nucleotides can then be digested using an exonuclease (e.g. phosphodiesterase) whereas the phosphorothioates are resistant to digestion. Exonuclease digestion takes a considerable amount of time and is not always quantitative.

Another method to shorten the products which have to be analyzed mass spectrometrically was proposed by Monforte et al. (J. A. Monforte, C. H. Becker, T. A. Shaler, D. J. Pollart, WO 96/37630). The authors introduce linkers into the primers which can be cleaved chemically or enzymatically. The introduction of chemicals, however, always has the disadvantage of introducing traces of impurities which again may form adducts. In addition, chemical cleavage needs adjustments of other parameters of the solution as for instance pH values, needing more chemicals to be added with the danger to introduce, e.g., alkali ions. Enzymatic cleaving, e.g. by restriction endonucleases, means a very restricted design of the primers which have to offer a recognition pattern for the nucleases and also needs adjusted buffer conditions for cleavage, making washing after cleavage a necessary step.

Sample preparation methods for mass spectrometric mutation analyses which are simpler and more reliable are therefore still being sought.

SUMMARY OF THE INVENTION

The invention provides simplified and reliable method for the rapid preparation of clean and short DNA samples for the analysis of gene material for previously known mutation sites by mass spectrometry. Favorably, the analysis procedure should show some multiplexing potential. The invention uses primers with photocleavable linkers. The linker forms a bridge over a base pair without inhibiting hybridization or enzymatic extension by polymerases. The linker allows the primer to be cleaved after extension in order to obtain short DNA fragments which can be more easily detected by mass spectrometry.

To this end, it is advantageous to make the chain products as short as possible by removing the greater part of the primer (which does not contain any information on the mutation) from the chain products. This reduces the molecular weight of the DNA chain products and increases the precision of the mass determination. It is also advantageous to neutralize largely the DNA chain products which carry information about the mutation being examined in the form of their molecular weight and to provide the products on a selective basis with charge carrying groups so that the products can be ionized in the MALDI or ESI process in preference with high sensitivity and selectively with respect to other components of the PCR reaction solution.

The invention consists of working with modified primers, instead of the primers which are usually used for the method of primer extension: Within a few nucleotides from the 3' position which is to be extended, the primers contain a photocleavable linker which is precisely as large to approximately bridge one nucleobase and does not significantly hinder either hybridization at the PCR-amplified template or enzymatic extension of the primer. After mutation-dependent extension of the primer has taken place, the linker is cleaved by UV light. In this process, very short cleavage fragments of the extended primer are generated which serve as products for the mass spectrometric measurements. The short cleavage fragments contain the information about the mutation. The length of the cleavage fragments may be selected at will from between approximately four to ten bases. Consequently, the weight of the DNA products which are to be measured ranges from approximately 1200 to 3000 atomic mass units. This is the best mass range both for MALDI and ESI mass spectrometers. These primary fragments can be analyzed very easily in a mass spectrometer, especially when the further modifications mentioned below are used. Both MALDI and ESI can be used.

As photocleavable linkers, building blocks from the o-nitrobenzyl derivatives class of compounds are particularly suitable. After converting the o-nitrobenzyl derivatives into activated phosphoramidites for automatic DNA synthesis (most likely β-cyanoethyl phosphoramidites), the photolinker can be incorporated at any position of the primer, replacing a regular nucleotide. Such o-nitrobenzyl derivatives do not interfere with hybridization and only slightly lower the optimum hybridization temperature during a DNA polymerase reaction. They are accepted by various polymerases as non-interfering the elongation at the 3' end if there are at least three nucleotides between 3' end and linker. The synthesis and mechanism of photocleavable 1-(2-nitrophenyl)ethyl esters of various different phosphates and thiophosphates have already been examined in detail by Walker et al. (*J. Am. Chem. Soc.* 1988, 110, 7170–7177) and by Ordoukhanian and Taylor (*J. Am. Chem. Soc.* 1995, 117, 9570–9571) but no application to mass spectrometry has been mentioned. It should be well understood that these linkers are by no means simple derivatives of nucleotides by just introducing other groups as bases.

If phosphorothioate nucleotides are inserted between the linker and the 3' position of a primer, then these can be alkylated either before or after the photocleavage and can therefore yield short modified oligomers with "peptide-like properties" from the point of MALDI-MS as the products. Mutation-dependent primer extension can be carried out very simply in this method by using four ddNTPs (equal-number-nucleotide primer extension), since the mass of these "peptide-like products" can be determined very well and the neutralized molecules do not form metal-ion adducts. It is therefore very easy to determine the differences from 9 to 40 atomic mass units.

If α-thiodideoxynucleoside triphosphates (α-S-ddNTPs) are used as terminators which are alkylated after the extension like the phosporothioate nucleotides, then it is possible to measure the products in the negative operating mode of the mass spectrometer since, during the decomposition, the photolinker generates a phosphate group with two negative charges at the 5' position of the test oligomer. Because one negative charge on the phosphate group is easily neutralized by the acid matrix (e.g. 3 HPA) in the gas phase, an oligomer with a single negative charge ultimately appears and this may be regarded as having been given a negative charge tag. It is also possible to use a method involving a positive charge tag. The charge can, for example, be attached by bonding a positively charged group to the α-S-ddNTP terminal positions or it can be bonded to one of the phosphorothioate nucleoside building blocks of the primer. Quaternary ammonium salts, for example, can be used to provide the positive charge.

Due to the high stability of the DNA products which are neutralized except for the charge tags and due to their freedom from adducts, the mass signals they produce are much sharper and have a better signal-to-noise ratio. Sensitivity is therefore increased and the mass determination is made easier.

The charge-neutralized variations of the equal-number-nucleotide primer extension method are therefore particularly suitable for multiplexing. Here, several possible mutations are examined simultaneously in a single sample. The mutations can be easily distinguished according to the lengths of the DNA products generated, usually even when the number of nucleotides is the same. This multiplexing procedure is familiar to the specialist. In this case, however, its application is particularly advantageous because, for normal DNA products, neutralization reduces the otherwise dramatic drop in sensitivity with their length and this means that parallel detection of the products is made easier. Due to the shift in product masses to a range of higher resolution, it is also possible to arrange the product masses more narrowly in the multiplex reactions.

Of course, the differential-number-nucleotide primary extension method as described can also be improved by using photocleavable linkers. It is also possible to use the equal-number-nucleotide primer extension method without further chemical modifications with increased reliability and increased multiplexing capability by photolytic shortening of the reaction products as described, since the very short DNA molecules have a much smaller tendency to form adducts because there is a significantly smaller number of negative charges.

As the specialist knows, primers can also be made labelled with biotin at the 5' end. With biotinylated extension primers containing linkers according to the invention, the cleaning process can be simplified. The test solutions with the extended primers, for example, are pipetted onto special anchor surfaces on the sample supports used for mass spectrometry. These anchor surfaces contain streptavidine which is covalently bonded to the support surface. The biotinylated positions of the products bond in a known manner to the streptavidin. It is now a very simple matter to wash the sample support with the samples attached and in this way, the polymerase, the excess ddNTPs, the buffers from the solutions used, the template and impurities can be washed away from all of the samples at the same time. After drying the sample support plate, the products can be subjected to photolytic cleavage. The biotinylated oligomers can alternatively be bonded to other streptavidine-coated surfaces, such as the bottoms of wells in microtitre plates. The cleavage products are then taken up from the wells with a matrix solution, crystallized out with the matrix substance on the sample support plate by drying and then measured using a mass spectrometer.

Apart from the biotin/streptavidine interaction, other mechanisms are also conceivable for bonding the linker-carrying primer to a surface, such as the reaction of a 5' amino group on the oligomer.

DETAILED DESCRIPTION

Figure 1:
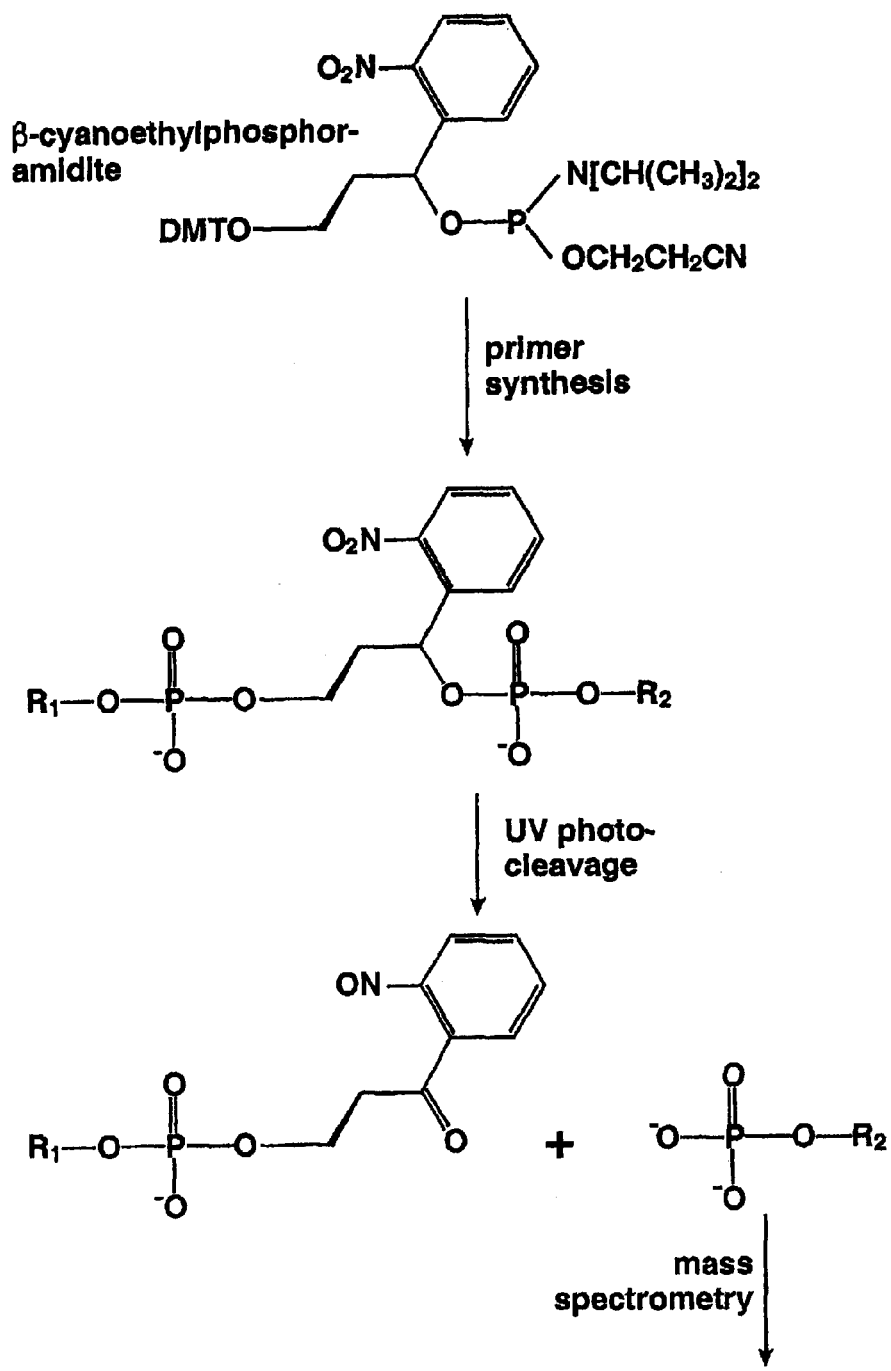
FIG. 1 shows the structure of the linker. The photocleavable β-cyanoethylphosporamidite of the o-nitrobenzyl derivative can be used to replace, during primer synthesis, a regular nucleotide. The linker bridges the neighboring nucleotides with approximately the same distance as a regular nucleotide, but containing a 1,3-propandiol moity instead of a sugar unit. Hybridization of the linker-containing primer to the complementary master template is possible with any counter-nucleotide, whereby the $R_2$ sequence is obtained as a monophosphate. $R_1$ and $R_2$ are the two DNA sequences upstream and down-stream from the linker. Cleavage produces the $R_2$ sequence for mass spectrometric measurements, whereby the $R_2$ sequence is bound to a phosphate group with doubly negative anion character. After protonation of these two anions in the MALDI process, the phosphate group adds 81 atomic mass units to the weight of the protonated $R_2$ sequence. (After UV-irradiation, a second cleavage product, not shown here, containing the R1 group is formed as the 3'-monophosphate).
Figure 2:
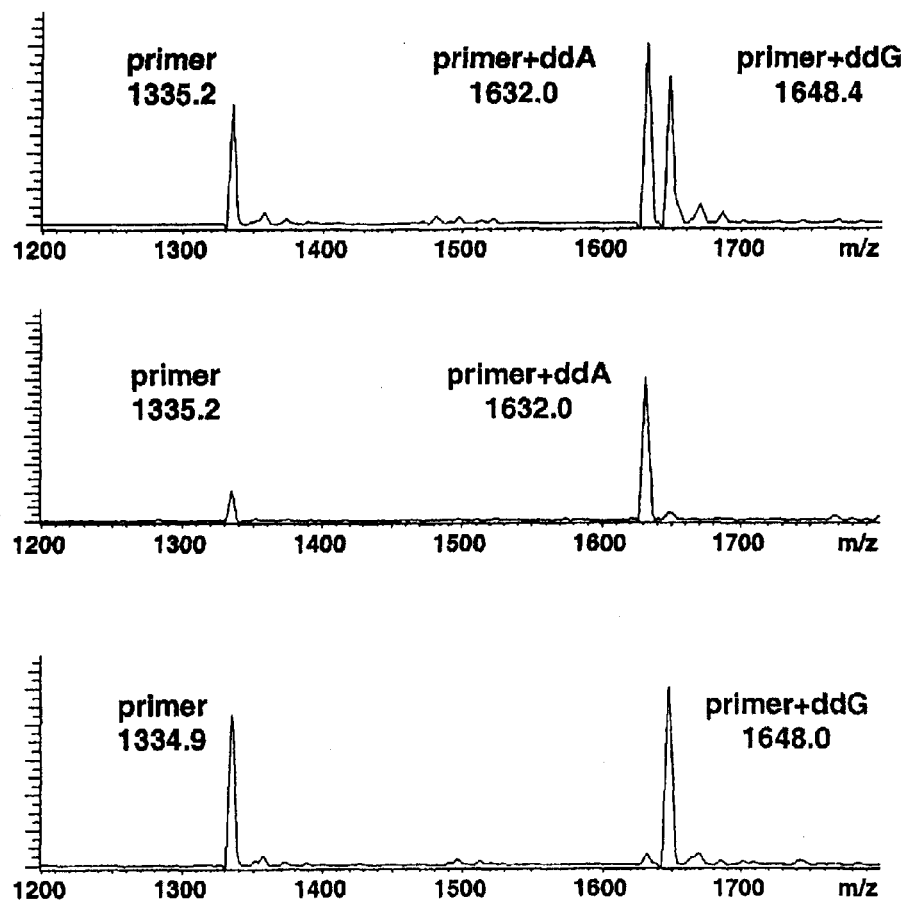
FIG. 2 exhibits three mass spectra of DNA pentamers, produced from samples obtained by primer extension and cleavage according to this invention (SNP PAI1). The upper spectrum shows the heterozygous case, the two lower spectra present the two homozygous cases. In all three spectra, the leftovers of the non-elongated extension primers are visible; these may serve as easy mass references.

One favorable embodiment is based on a biotinylated primer with a photocleavable linker according to the invention which is extended by exactly one base. The method consists of the following steps:

First of all, a selection primer pair or primary primer pair is selected, made or purchased for amplifying a DNA product by PCR. These primary primers enclose the possible mutation site (or sites) over a relatively wide range. Using appropriate software programs if necessary, they are selected so that PCR amplification can be carried out using a standard procedure, i.e. by using the same process parameters for all samples. The primers can be ordered from specialist companies who need to be informed about the sequence. These selection-primer pairs are used to make enough templates to be used as the master templates for primer extension.

After this, the extension primers (or secondary primers) are determined. It must be possible to attach them directly next to the possible mutation site. They contain a biotinylated 5' position, a chain of approximately 10 to 20 standard nucleotides, a photocleavable linker according to the invention and approximately 3 to 7 other nucleotides up to the 3' position. These primers can also be made by specialist companies who need to be supplied with specialized data (with the possible provision of the linker triphosphates).

After amplifying a DNA sequence by PCR using the selected primer pairs, the PCR solution is cleaned from the dNTP building blocks using, for example, the enzymatic digestion of the dNTPs followed by thermal deactivation of the digestion enzyme. After adding the extension primer and the terminating ddNTPs and a suitable DNA polymerase, extension of the primers is started by the usual temperature cycles. The temperature cycle for extension is repeated several times since extension is not always successful during the first stage.

If the extension primers are largely consumed by the extension process, then the uncleaned PCR solution with the extended primers is mixed with a bonding buffer and pipetted onto the anchors containing the streptavidine on the sample support plate, the biotinylated positions of the extended primer bonding to the streptavidin. By the appropriate washing procedure, all components of the PCR solution, the buffer, the unused ddNTPs, the templates, the remaining primary primers, the enzymes and the salts can now be removed by washing all the samples together. Many different samples can be attached to a single sample support plate and washed at the same time. The sample support plate is then dried. The dried sample support plate is now radiated with UV light to cleave the linkers. The cleavage period lasts from 5 to 30 minutes depending on the strength of the UV light. Subsequently, a solution of a MALDI matrix, e.g. 3-hydroxypicolinic acid, is applied and the plate is dried again. During this time, the matrix crystallizes out and the DNA cleavage products which are separated from the primers are incorporated in the tiny crystals. The samples on the sample support are then subjected to analysis in a MALDI mass spectrometer. A part of the matrix together with the analyte molecules is vaporized in a laser shot and molecules with preferably one positive or negative charge are produced by the transference of protons from the 3-HPA matrix to the DNA molecules. The mass of the molecules can be determined in a MALDI TOF mass spectrometer in the appropriate operating mode. The measurement is finished with a mass determination and the assignment of the sample to wild type or known mutant.

The sample preparation for analysis using electrospray ionization mass spectrometry can be carried out in a similar way. In this case, the samples are not dried and all the steps of the procedure are carried out in the solution. Bonding to the surface-bound streptavidin, for example, can take place in a known way by using magnetic beads or the cavities of a microtitre plate with streptavidine bonded to the surfaces. In order to wash the product, the magnetic beads can be arrested magnetically on the walls of the cleaning vessels, such as the wells of microtitre plates.

Another version of the method uses primers which have some phosphothioates neighboring the 3' position and α-thiodideoxynucleoside triphosphate terminators and this involves alkylation of the phosphorothioates following primer extension in order to neutralize the DNA fragments being measured. It is then particularly beneficial to use nucleoside triphosphate derivatives such as these which have already been provided with a positively charged group such as a quaternary ammonium group as the charge tag. The charge-carrying group can also be attached to the phosphorothioate nucleotides of the extended primer, especially favorably at the second, third or fourth base counting from the 3' position. In this type of method, fixing, cleaning and photocleavage on the solid phase is made superfluous since the neutralized DNA fragments which have been provided with a charge tag and shortened by photocleavage, can be measured from the reaction batch without further cleaning because the sensitivity has been increased by a factor of 100.

The method consists of the following steps:

First of all, the selection primer pair or primary primer pair for amplifying the DNA product by PCR is again selected so that the corresponding product from PCR amplification contains the mutation site. The extension primers or secondary primers are then determined. It must be possible for them to be attached next to the possible mutation site. They contain a chain of 10 to 20 standard nucleotides at the 5' position, after that, a photocleavable linker according to the invention and approximately 3 to 7 phosphorothioate nucleotides up to the 3' position.

After the DNA target sequence has been amplified by PCR, the remaining dNTPs are removed by enzymatic digestion and the digestion enzyme is thermally deactivated. Extension primers, ddNTP terminators, a suitable DNA polymerase (such as thermosequenase) and a buffer which is adjusted to the enzyme are added. Specific primer extension is carried out in a temperature cycle which is repeated several times. α-thiodideoxynucleoside triphosphates (α-S ddNTPs) are preferred for the extension. Next, the phosphorothioate compounds are neutralized by alkylation. After the solution has been applied to the support plate coated with the matrix, this is radiated with UV light whereupon the photocleavable linker breaks. Due to the linker breaking, a phosphate group at the 5' position of the alkylated phosphorothioate fragment which will impart a double negative charge to the molecule will be left behind. The mass can therefore be determined in a MALDI TOF mass spectrometer in negative mode since one negative charge on the phosphate group can be neutralized by the acid matrix (e.g. 3-HPA) in the gas phase. Alternatively, a positive charge (charge tag) can be attached within the phosphorothioate part of the extension primer and the products can be measured in positive mode.

However, the invention is not restricted to equal-number-nucleotide primer extension but can also be applied to the differential-number-nucleotide primer extension. As before, using the photocleavable linker simplifies the method. A variant with a primer is also possible which in some cases contains phosphorothioate compounds and after extension is neutralized by alkylation.

A favorable method may appear as follows:

For the initial PCR amplification, the selection primers must be chosen so that the known point mutations, insertions and deletions which are to be analyzed are located within the PCR product generated.

It is favorable to then remove the nucleotides left over from PCR amplification by using known methods, such as the "nucleotide removal kit" supplied by QIAGEN. Alternatively, the residual nucleotides can be decomposed by using an alkaline phosphatase and the solution processed without any further cleaning.

Next, apart from the extension primers with phosphorothioate bonds at the end, which have been provided with linkers according to the invention, a reduced set of modified deoxynucleoside triphosphates (such as α-S nucleotides or α-Me nucleotides) are added, in which the nucleotide is missing at which the chain extension specifically for the mutation should stop. This position must be selected so that the molecular weight of the product chain will supply information about the mutation type. As an extension to this, one or more dideoxynucleoside triphosphate terminators can be added which do not exist as deoxynucleoside triphosphates. This is how mutation-specific chain-termination products are formed.

After their incorporation into the DNA chain by the polymerization, the α-S nucleotides can be easily neutralized using a method such as alkylation, particularly methylation.

The extension primer should already have a positive charge tag. The charge tag is preferably attached near to the 3' position of the primer. The sugar-phosphate backbone between the 3' position and the charge tag should be selected so that it can be charge-neutralized.

The newly added extension primers are now attached to each of the strands of the PCR products serving as templates and then extended by enzymatic replication.

After this, the DNA chain products are shortened by photolyzing the linkers with UV light. Chemical preparation then takes place giving rise to products, neutralized and provided with charge tags, which are particularly easy to ionize using MALDI.

Using charge tags, of course, only makes sense if all the residual charges are removed from the DNA products in the process, since it is only then that the charge state of the analyte molecule can be fully defined. By charge tagging and neutralizing the residual DNA, the sensitivity is improved by a factor of 100 and matrices can be used which selectively support the ionized desorption of these modifications so that it is possible to carry out the mass spectrometric analysis without cleaning up.

DNA has a polyanionic backbone. By using sulphurized internucleotide cyanoethyl phosphite bonds of the primer nucleotides between the linker and the 3' position forming phosphorothioate nucleotides, a chemical function is produced in which the negative charge can be removed using simple chemistry, e.g. by alkylation. Neutralizing the DNA not only contributes to raising the ionization yield but also suppresses the formation of adducts and helps to stabilize the DNA in the MALDI process.

On the one hand, the potential of this method lies in its ability to increase sensitivity and reduce adduct formation by the modifications implemented. On the other hand, certain classes of substances can be selectively promoted in MALDI mass spectrometry so that undesirable reaction side products can be screened out.

In practice, this means that the relevant products can be analyzed exclusively due to the modifications which have been introduced and the choice of mass-spectrometric parameters which is made. The template DNA, for example, can be screened out completely and therefore does not have to be removed in a cleaning process. This also increases the possibility of multiplexing. The whole process can be carried out with very little or no cleaning after the enzymatic and chemical reaction stages.

Of course, it is also possible to improve cleaning by introducing biotin at the 5' position of the primer.

By appropriate primer design, cut functions and various distances to the point-mutation sites which are familiar to every specialist working in this area, several point-mutation sites can be analyzed simultaneously in a so-called multiplex analysis. Indeed, these sites can be analyzed on both sides of the DNA strands of the DNA double strand, i.e. in counter orientation; an internal result control is produced and, therefore, a high level of analytical reliability.

Not only can the analysis of a single PCR product be carried out in multiple ways but a multiplex analysis can also be carried out simultaneously with a set of several PCR products which have been amplified in a single multiplex PCR process. Different parts of a genome are amplified simultaneously in a multiplexed PCR. After this, the analysis can be carried out on each PCR product with the necessary number of primers. The method is particularly straightforward for equal-base-number primer extensions.

For differential-nucleotide primer extensions, it is essential that each analysis is carried out with the same combination of nucleotides. This has to be taken into account when planning and elaborating the multiplex analyses. In principle, all the information required about the mutations in a genome DNA can be scanned by using a combination of four nucleotide systems.

What is claimed is:

1. A method for mass-spectrometric analysis of a known mutation site in genome DNA, the method comprising:
   providing an extension primer having a nucleotide chain that contains a photocleavable linker and attaching the primer to the DNA adjacent to the mutation site;
   extending the primer using mutation dependent primer extension with a complementary mixture of non-terminating and terminating nucleoside triphosphate derivatives, said mixture having a ratio of one non-terminating to three terminating nucleoside triphosphate derivatives, or two non-terminating to two terminating nucleoside triphosphate derivatives, the terminating nucleoside triphosphate derivatives terminating the extension at one of a plurality of predetermined lengths;
   cleaving the photocleavable linker with UV light irradiation to produce a DNA cleavage product; and
   analyzing the DNA cleavage product using mass spectrometric analysis to determine the nucleotide present at the mutation site.

2. A method as in claim 1, wherein the linker is located 3 to 10 bases from the 3' position of the primer.

3. A method as in claim 1, wherein the linker is derived from the class of chemical compounds known as o-nitrobenzyl derivatives.

4. A method as in claim 1, wherein the extension is carried out by using a mixture of four types of nucleoside triphosphate derivative terminators so that extension only takes place by precisely one base.

5. A method as in claim 4, wherein dideoxynucleoside triphosphates are used as the nucleoside triphosphate derivative terminators.

6. A method as in claim 1, wherein an internucleotide cyanoethyl phosphite bond of the primer nucleotides between the linker and the 3' position is sulphurized forming phosphorotioate nucleotides, and wherein the phosphorotioate nucleotides are alkylated before analysis by mass spectrometry.

7. A method as in claim 6, wherein the extension is carried out with a complementary mixture of terminating and non-terminating nucleoside triphosphate derivatives and negatively charged ions are measured in the mass spectrometer.

8. A method as in claim 7, wherein dideoxynucleoside triphosphates are used as nucleoside triphosphate derivative terminators.

9. A method as in claim 8, wherein the extension is carried out with a complementary mixture of terminating and non-terminating nucleoside triphosphate derivatives in which the nucleotide that is inserted, like the phosphorothioate nucleotides of the primer, is alkylated before analysis by mass spectrometry and the negative ions are measured in the mass spectrometer.

10. A method as in claim 9, wherein α-thiodideoxynucleoside triphosphates are used as the nucleoside triphosphate derivative terminators.

11. A method as in claim 10, wherein each one of the α-thionucleoside trihosphate derivative terminators carries a chemical group with a positive charge in addition.

12. A method as in claim 9, wherein one of the phosphorothioate nucleotides of the extension primer carries a chemical group with a positive charge.

13. A method as in claim 12, wherein the chemical group carrying the charge is located on the second, third or fourth nucleobase counting from the 3' position.

14. A method as in claim 11, wherein a chemical group carrying the charge is a quaternary ammonium group.

15. A method as in claim 9, wherein the primer for the primer extension carries an anchor for the attachment of a charge group which is attached before the analysis by mass spectrometry is carried out.

16. A method as in claim 15, wherein the anchor carries a free amino group.

17. A method as in claim 1, wherein ionization in the mass-spectrometric mass determination is achieved by using matrix-assisted laser desorption and ionization (MALDI).

18. A method as in claim 11, wherein ionization in the mass-spectrometric mass determination is achieved by using matrix-assisted laser desorption and ionization (MALDI), and wherein a matrix is used which does not contribute to the transfer of charge to the DNA products being measured.

19. A method as in claim 18, wherein α-cyano-4-hydroxycinnamic acid methyl ester is used as the matrix.

20. A method as in claim 1, wherein the 5' position of the extension primer is biotinylated.

21. A method as in claim 20, wherein the primer, after extension, is bonded via biotin to a streptavidin molecule that is fixed to a surface for the purpose of purging all the components of reaction fluid that was required for the extension.

22. A method as in claim 21, wherein the streptavidin is bonded to a surface of a sample support which is also used for further mass-spectrometric analysis.

23. A method for mass-spectrometric analysis of a known mutation site in genome DNA, the method comprising:
   providing an extension primer having a nucleotide chain that contains a photocleavable linker and attaching the primer to the DNA adjacent to the mutation site;
   extending the primer using mutation dependent primer extension, the primer extension using at least one chain terminator that terminates the extension at one of a plurality of predetermined lengths, wherein the extension uses a complementary mixture of fewer than four non-terminating and terminating nucleoside triphosphate derivatives and is carried out such that the predetermined lengths differ by at least one base;
   cleaving the photocleavable linker with UV light radiation to produce a DNA cleavage product; and
   analyzing the DNA cleavage product using mass spectrometric analysis to determine the nucleotide present at the mutation site.

24. A method as in claim 23, wherein the linker is located 3 to 10 bases from the 3' position of the primer.

25. A method as in claim 23, wherein dideoxynucleoside triphosphates are used as the nucleoside triphophate derivative terminators.

26. A method as in claim 23, wherein the 5' position of the extension primer is biotinylated.

27. A method as in claim 26, wherein the primer, after extension, is bonded via biotin to a streptavidin molecule that is fixed to a surface for the purpose of purging all the components of reaction fluid that was required for the extension.

28. A method as in claim 27, wherein the streptavidin is bonded to a surface of a sample support which is also used for further mass-spectrometric analysis.

* * * * *

UNITED STATES PATENT AND TRADEMARK OFFICE
CERTIFICATE OF CORRECTION

PATENT NO. : 7,160,680 B2  
APPLICATION NO. : 10/079043  
DATED : January 9, 2007  
INVENTOR(S) : Felix Hausch et al.

Page 1 of 1

It is certified that error appears in the above-identified patent and that said Letters Patent is hereby corrected as shown below:

Column 11, Line 29, please delete "by using a mixture of four types of nucleoside triphosaphate derivative terminators".
Column 11, Lines 58, please replace both words "phosphorotioate" with --phosphorothioate--.
Column 12, Line 12, please replace "trihosphate" with --triphospate--.
Column 12, Line 61, please replace "radiation" with --irradiation--.

Signed and Sealed this

Seventeenth Day of June, 2008

JON W. DUDAS
*Director of the United States Patent and Trademark Office*